United States Patent [19]

Skurkovich et al.

[11] Patent Number: 4,490,357

[45] Date of Patent: Dec. 25, 1984

[54] SIMPLIFIED IN-VITRO INTERFERON PRODUCTION

[76] Inventors: Simon V. Skurkovich; Boris Skurkovich, both of 261 Congressional La., #709, Rockville, Md. 20852

[21] Appl. No.: 335,699

[22] Filed: Dec. 30, 1981

[51] Int. Cl.$^3$ .................... A61K 45/02; C12P 21/00
[52] U.S. Cl. ........................ 424/85; 435/68; 260/112 R
[58] Field of Search ............... 424/85; 260/112 R; 435/68, 811, 2

[56] References Cited

U.S. PATENT DOCUMENTS

| | | | |
|---|---|---|---|
| 3,560,611 | 2/1971 | Chany et al. | 424/85 |
| 3,699,222 | 10/1972 | Isaacs et al. | 424/85 |
| 3,800,035 | 3/1974 | Goore | 424/85 |
| 3,910,824 | 10/1974 | Cartwright et al. | 424/85 |
| 3,975,344 | 8/1976 | Schwartz | 260/112 R |
| 4,198,479 | 4/1980 | Tytell et al. | 435/2 |
| 4,266,024 | 5/1981 | Swetly et al. | 435/68 |
| 4,279,892 | 7/1981 | Ishida et al. | 424/85 |
| 4,382,027 | 5/1983 | Braude | 424/85 |

OTHER PUBLICATIONS

Mogensen, K., et al., Pharm. Ther. A., vol. 1, pp. 369–381, 1977.
Interferons and Their Actions, W. E. Stewart II, editor, Havell, "Cellular Regulatory Mechanisms Controlling Synthesis of Interferons", pp. 37–38, 1977.

*Primary Examiner*—Blondel Hazel
*Attorney, Agent, or Firm*—Wells & Wells

[57] ABSTRACT

Interferon is produced in-vitro from whole blood, obtainable from animals or humans including blood from corpses or retroplacental blood, in a simplified non-critical process preferably carried out in a sterile system of interconnected plastic bags. The blood is stabilized and innoculated with an interferon inducer before culturing in an incubator. This results in interferon containing blood useful directly for transfusions or further processable to obtain a variety of therapeutic interferon containing preparations including plasma, serum and albumin in accordance with disclosed phases of this invention. Interferon carrying plasma is thus separated and treated further to isolate interferon carrying serum or albumin, if desired. In-vivo innoculation to produce antibodies before taking blood provides improved disease fighting characteristics in the derived product. Steps are provided for purification of the products such as removal of residual inducers or the treatment for presence of suspected hepatitis virus, etc.

25 Claims, 5 Drawing Figures

SIMPLIFIED IN-VITRO INTERFERON PRODUCTION

TECHNICAL FIELD

This invention relates to the production of interferon and more particularly it relates to in-vitro production of ready to use interferon preparations from whole blood.

BACKGROUND ART

The in-vitro culture and separation of interferon is well established in the art. The fundamental process is described in U.S. Pat. No. 3,699,222 - A. Isaacs et al., Oct. 17, 1972. However, in the prior art production techniques very critical preparation of tissue used to culture the interferon has limited production and necessitated close and careful controls. For example, leukocytes, lymphoblasts and fibroblasts must be carefully prepared before the interferon culture process can begin in the most prominent and successful types of in-vitro interferon culture, as for example, set forth in U.S. Pat. Nos. 4,266,024 - P. Swetly, May 5, 1981 or 4,198,479 - A. A. Tytell et al., Apr. 15, 1980.

In these prior art in-vitro culture processes various sorts of interferon inducer substances are known and new ones are being developed as exemplified by U.S. Pat. No. 4,279,892 - N. Ishida et al., Jul. 21, 1981. Also steps taken in purification or isolation of the cultured interferon is known in the art as exemplified in U.S. Pat. No. 3,975,344 - A. A. Schwartz, Aug. 17, 1976.

It has been considered in the past that interferon could only be made in-vitro with leukocytes isolated from blood and not with whole blood.

Thus, the prior art has necessitated the expensive and time consuming steps of deriving from blood by centrifuging and precipitation in the presence of expensive chemical and biological materials selected cells, e.g. leukocytes.

Furthermore, in the prior art production of interferon many refining steps are required to recover the interferon. These steps are also expensive and time consuming.

Also the interferon thus produced by prior art techniques need be carefully administered to patients requiring expert skills as to proper dosages and conditions of administration.

It is therefore an objective of this invention to provide improved, simplified methods of producing interferon that are adaptable to large scale production with the product available in a ready to use range of interferon containing preparations suitable for instant use or storage, as the case may require. Other objects, features and advantages will be found throughout the following description, drawings and claims.

DISCLOSURE OF THE INVENTION

Fresh blood taken from a healthy donor is stabilized with an anticoagulant such as citrate phosphate dextrose adenine solution and is treated in-vitro with an interferon inducer. Thereafter the blood is incubated until interferon titers approach their peak.

A range of output interferon containing preparations are thus made available. The process, for example, makes available interferon containing whole blood for administration by transfusion in a most simplified production process. By removing cells another easily administered interferon containing product is produced in the form of plasma. Further processing can result in albumin containing interferon or other forms of refined interferon that can be frozen, freeze dried and stored for long times.

Improved quantities of output interferon are obtained by adding small amounts of interferon to the stabilizing solution and culturing in the blood in a priming step for about two hours before adding the interferon inducer and culturing in the main culture step.

The entire process can be carried out in a sterile system of interconnected plastic bags for example to provide blood or plasma in transfusion dose sizes ready for immediate use, or on a large scale for production quantities.

BRIEF DESCRIPTION OF THE DRAWING

The various drawing figures shown in block diagram form the system interrelationships using whole blood as the culture medium for achieving in-vitro production of a range of interferon containing preparations, as afforded by this invention.

THE PREFERRED EMBODIMENT

Figure 1:
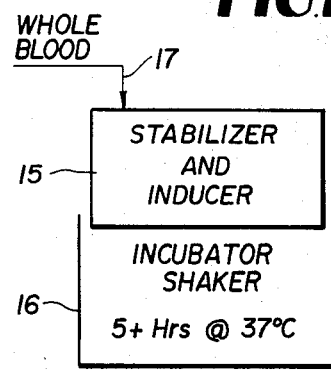
FIG. 1 shows a production process afforded by this invention for interferon containing whole blood that is ready to use for direct transfusion.

Although it has been considered necessary heretofore in in-vitro production of interferon to isolate and concentrate blood cells such as leukocytes in pre-culture steps in order to produce interferon by cell culture steps, it has been found by this invention that contrary to past published practice and opinion, fresh whole blood will produce interferon in-vitro.

The blood can be taken from healthy donors, animal or humans. In humans retro-placental blood may be used as well as blood from a slaughtered animal. Blood can be taken from a corpse not later than six hours after death.

For a low cost sterile system capable of batch lot or quantity production the blood is preferably processed in an interconnected plastic bag closed system using the type of containers obtainable from Fenwal Laboratories, Deerfield, Ill. 60015. Other vessels may be used.

The invention may be better understood by reference to the drawing wherein various steps of the process for obtaining interferon preparations are illustrated.

With reference to FIG. 1, a vessel, preferably a plastic bag, 15 is used to produce in-vitro interferon containing blood which can be used directly (from the bag) for transfusion. The interferon is obtained by culturing whole blood in-vitro in the vessel 15 by means of the incubator-shaker 16.

Thus, the whole blood is introduced at 17 into bag 15 containing additives including a stabilizer (anticoagulant) such as citrate phosphate dextrose adenine solution, heparin or the like. It may also be passed through an ion-exchanging column which selectively removes calcium ions. Also an interferon inducer such as killed virus, for example NDV, bacterial inducers or synthetic inducers is entered into the bag 15. The blood is then agitated and incubated by placing bag 15 into device 16 typically for 5 to 48 hours depending upon the inducer, blood (which differs from different animals), etc. at about 37° C. to induce interferon and the incubation is terminated when the interferon titers are approaching a peak. The agitation may be achieved by rotation or shaking at approximately 7 to 15 times per minute.

After this simple procedure therefore the interferon containing blood is stored at 4° C. as an interferon preparation usable as a therapeutic agent by direct transfusion, under the usual conditions of matching blood types, etc.

Figure 2:
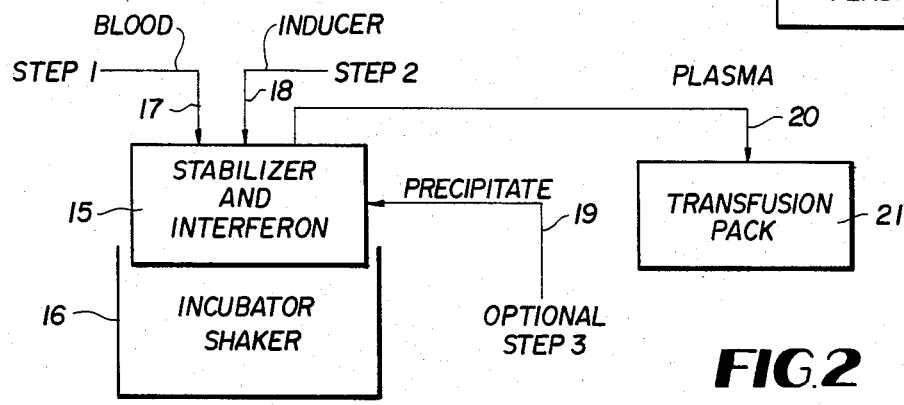
FIG. 2 shows amplified production process interrelationships for obtaining an interferon containing product ready to use for direct transfusion.

Extensions of this simple process are illustrated by FIG. 2.

For a better yield of interferon by an alternative process, a priming culture step is taken by adding a small amount of interferon or other primer into the vessel 15 with the stabilizer, e.g. ten to 60 units of interferon per ml of blood added at 17, and then pre-incubating for about two hours at 37° C. before adding the interferon inducer at 18 and proceeding with the culture process as above-described.

The incubated culture (blood), if not used as the desired interferon preparation, then may be centrifuged by placing bag 15 into device 19, until all blood cells are precipitated. Then the interferon containing plasma is mechanically driven out of bag 15 along connector tubing 20 into bag 21. The plasma may be used for transfusion or stored for later use. Alternatively the precipitation can be accomplished by retaining bag 15 in stable position for 1.5 to 2 hours until the cells precipitate. Other plasmaphereses steps could be used.

Figure 3:
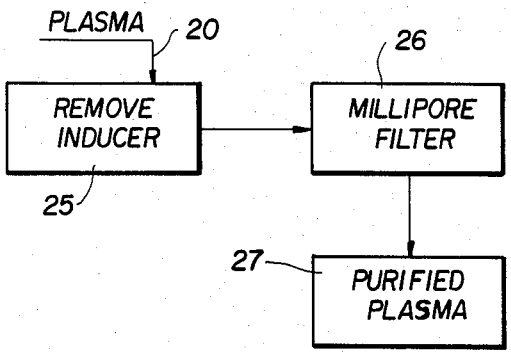
FIG. 3 shows a series of production process steps for purifying interferon containing plasma.

The presence of many interferon inducers in interferon containing blood or plasma does not endanger their administration by transfusion. In the case of plasma only small amounts of inducer may be present in any event. If, however, it is desirable to remove any small amount of inducer that might be present the steps illustrated in connection with FIG. 3 may be taken.

Thus, for example, the plasma is passed through an immunosorbent substance, such as generally used in purification of interferon, containing immobilized antibodies to these inducers to extract any residua or inducer. This is particularly suitable for human use. For use in animals a small amount of highly active antibodies against the particular inducer used for inducing the interferon is added to the plasma. The inducer precipitates and the precipitate is isolated by driving the plasma from vessel 25 through millipore filter 26 to obtain inducer free interferon containing plasma in vessel 27. The interferon preparation consisting of plasma with interferon may be frozen at $-35°$ C. or freeze dried for storage and later use.

If the inducer is dialyzable, it may be removed from the plasma by dialysis against a sterile isotonic saline solution pH 7.2–7.4.

Figure 4:
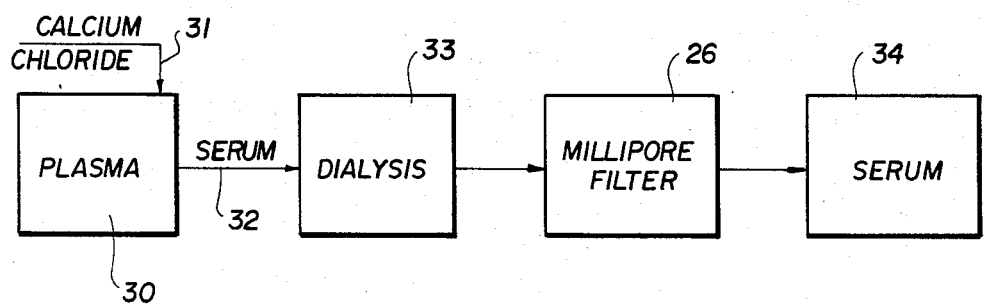
FIG. 4 shows a series of production process steps for preparing interferon containing serum as the interferon containing preparation.

If interferon containing serum is the desired interferon preparation, interferon containing plasma is further processed as shown in FIG. 4 by entry into vessel 30 with a 30% solution of calcium chloride 31 (1.5 ml per liter of plasma). This leads to precipitation of fibrine. The interferon containing serum 32 is then dialyzed at 33 against a sterile isotonic saline solution pH 7.2–7.4 and passed through millipore filter 26 to obtain the interferon containing serum 34 preparation which may be stored by freezing or freeze drying.

Figure 5:
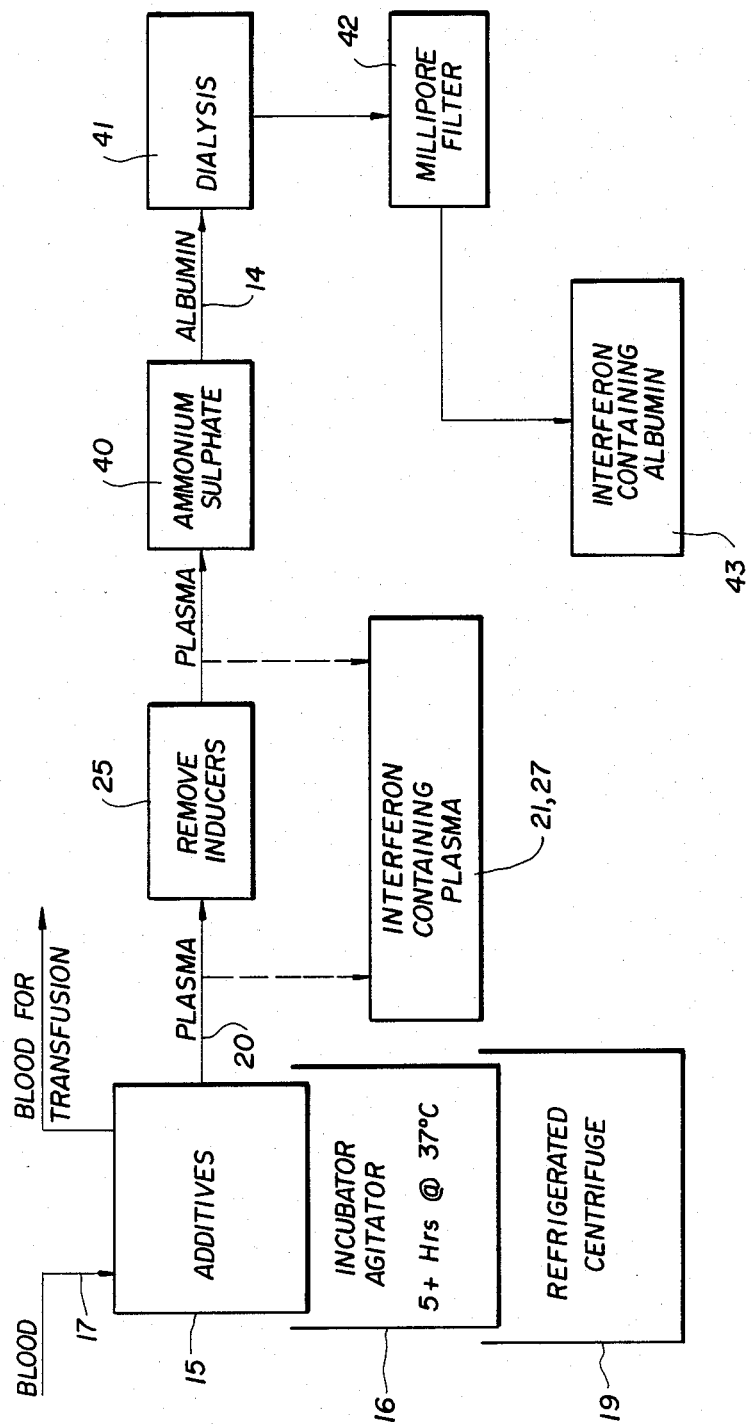
FIG. 5 is a comprehensive system diagram for production of interferon containing albumin in accordance with this invention.

In the more comprehensive system-process view of FIG. 5, the foregoing procedures and system elements are identified by similar reference characters for ready comparison.

If interferon containing albumin is desired the plasma is furtherprocessed by entry into vessel 40 with a 50% saturated ammonium sulphate solution which leads to precipitation of globulins. Then the interferon containing albumin is transferred through tubing 14 and dialyzed at 41 against a sterile isotonic saline solution with pH 7.2–7.4.

For sterilization the albumin is then passed into the millipore filter 42 to produce the end product 43. Other methods of isolation and sterilizing the albumin may be used if desired. The harvested albumin containing interferon 43 then may be frozen at $-35°$ C. or freeze dried for later use.

If pure interferon is desired it may be removed from the plasma by specific immunosorbents or by other methods. Also concentrated interferon preparations may be prepared if desired.

Having therefore more generally set forth the process steps afforded by this invention, the invention is set forth in more detail in the following examples.

EXAMPLE 1 - STABILIZERS

In the foregoing process the dose of the stabilizers is exemplified as follows:
(a) 10 ml 3.5% sodium citrate per 90 ml of blood/or
(b) anticoagulant citrate phosphate dextrose adenine solution 63 ml per 450 ml of blood. The 63 ml of solution contains 2.0 g dextrose (hydrous), 1.66 g sodium citrate (hydrous), 206 mg citric acid (hydrous), 140 mg sodium biphosphate, 17.3 mg adenine, or
(c) the same as (a) plus chloramphenicol - 0.075 g. The antibiotic is added in case of possible contamination of the blood, especially when retro-placental blood is used. Other antibiotics or chemotherapeutic agents can be used.

EXAMPLE 2 - INDUCERS

The inducers are NDV (Newcastle Disease Virus), and Sendai virus; synthetic inducers, e.g., Poly I: Poly C; bacteria or bacterial products, e.g. Brucella abortus; mitogens, e.g. phytohemagglutinin (PHA), concanavalin A (Con A), staphylococcal enterotoxin A (SEA) and nucleic acids, for example.

NDV - 10 to 100 viral particles for each leukocyte in the whole blood.

Poly I: Poly C - 10.5 microgram per $10^7$ leukocytes in the whole blood.

SEA - 0.001 microgram to 10 microgram per $1.5 \times 10^7$ leukocytes in the whole blood, more specifically.

0.01 to 10 microgram per $1.5 \times 10^7$ cells to induce 644 to 1323 units per ml in 48 hours in appropriate human blood.

EXAMPLE 3 - INCUBATION

The incubation proceeds until the minimum interferon titer is at least 128 dilution units per ml.

EXAMPLE 4 - BLOOD

Blood can be selected from human donors on the same criteria as used for transfusions.

In meat animals and poultry blood can be taken from any animals who meet veterinary requirements for use in preparation of food.

In camels, horses, cattle, cats, dogs, fur bearing or other wild or domestic animals, blood is taken from healthy animals.

For retroplacental human blood the puerpera should be healthy.

Blood meeting the other requirements for transfusion from corpses of healthy people before 50 years of age who died of incidental causes (trauma of head or vital organs) is taken not later than six hours after death.

Lymph or lymphocide containing organs suspended in plasma or lymph is used and defined as blood for the purpose of this invention. It is obtained from thoracic lymph duct of the slaughtered animal and introduced in the bag with the stabilizer and interferon inducer in the same dosage as whole blood.

Blood as defined herein also includes bursa of Fabricius in young birds, as are diluted in medium or serum of that particular species of bird to reach the concentration of about $5 \times 10^6$ cells per ml of liquid.

EXAMPLE 5 - DIALYSIS

Inducers may be isolated from the plasma by dialysis against the isotonic saline, pH 7.2–7.4 at 4° C. over 24 to 36 hours.

EXAMPLE 6 - STERILIZATION OF PLASMA, SERUM AND ALBUMIN

Millipore filters for sterilization having pore sizes of 0.22 microns commercially available are used.

EXAMPLE 7 - COMBINED ANTIBACTERIAL ANTIVIRAL AGENTS

A further advantage of the present method is the ability to produce a combined antibacterial and antiviral (interferon and specific antibodies) agent. This is most important because a patient suffering from a viral attack is then more subject to bacterial infections as a side effect. The combined agent therefore prevents the likelihood of a bacterial attack following or concurrent with a viral attack. It is particularly useful if the blood of animals is obtained at slaughter to administer substances that generate in-vivo specific antitoxic or antibacterial antibodies against the toxins or bacteria of the type likely to be present with a virus which is treated with interferon. Thus innoculations are made in-vivo ten days to six weeks before the blood is taken and the resulting plasma obtained by the foregoing process will have combined antiviral, and antibacterial or antitoxic properties. The following are useful in this respect: staphylococcal toxoid, E.coli bacteria, and pseudomonas aeruginosa toxoid.

A preferred bacterial innoculation would be an antigen used for immunization that also induces interferon.

Thus, the plasma will contain both specific antibodies and immune interferon. A preferred virus innoculation is with the same virus as used in the interferon inducer, so that the plasma contains both specific antiviral antibodies and immune interferon for more effective antiviral protection.

EXAMPLE 8 - DECONTAMINATION

In cases that contamination with live virus, e.g. hepatitis, is suspected in humans and animals, interferon containing plasma, serum or albumin is irradiated with ultraviolet or gamma radiation.

EXAMPLE 9 - IN-VITRO SIMPLIFIED PROCESS

Interferon is obtained in whole fresh blood treated as in Examples 1 and 4 and cultured in-vitro in the presence of an interferon inducer agent as in Example 2 for at least five hours at 37° C. to produce an interferon preparation constituting interferon containing blood which can be used directly for transfusion.

EXAMPLE 10 - IN-VITRO PLASMA PROCESS

Same as 9 with whole blood centrifuged or precipitated to produce interferon containing plasma.

EXAMPLE 11 - PURIFIED PLASMA PROCESS

Same as 10 with plasma treated to remove any residual inducers by passing the plasma through an immunosorbent containing immobilized antibodies to the inducer used in Example 9.

EXAMPLE 12 - INTERFERON CONTAINING ALBUMIN

Same as Examples 10 or 11 with further processing of the plasma to isolate interferon containing albumin.

EXAMPLE 13 - INTERFERON CONTAINING SERUM

Same as Examples 10 or 11 with further processing of the plasma in the presence of a calcium chloride 30% solution and dialyzing to obtain the interferon containing serum.

EXAMPLE 14 - PRODUCT STORAGE

The interferon containing plasma, serum and albumin preparations obtained in the foregoing examples are frozen at −35° C. and preserved for later use as required. Alternatively the preparations are freeze dried.

Thus, in accordance with this invention, by processing blood in-vitro to obtain interferon containing products (blood, plasma, serum, albumin, etc.) these products may be used directly for transfusion without modification, and may in some cases be stored for later use.

INDUSTRIAL USE

A simplified low-cost uncritical in-vitro method of production of interferon is afforded by this invention using whole blood as the culture medium to obtain a range of interferon preparations including whole blood and plasma, and plasma, serum and albumin all of which can be used immediately for transfusion and some of which may be frozen or freeze dried for later use.

We claim:

1. In a process comprising introducing an interferon inducing substance into in-vitro culture of leukocytes isolated from whole blood, incubating said culture under conditions producing interferon and separating an interferon-containing preparation from said incubated culture, the improvement comprising said in-vitro culture comprising said whole blood.

2. The process of claim 1 wherein the process is carried out in a closed sterile system comprising a plurality of interconnected plastic bags.

3. The process of claim 1 including the additional step of introducing into the blood stabilizers for maintaining the blood in a condition favoring the production of interferon during the incubation process.

4. The process of claim 3 including the further step of entering the blood stabilizers and inducing substance into a vessel before the whole blood is deposited.

5. The process of claim 1 including an initial container in said system for depositing the blood, wherein the blood stabilizers are introduced in solution into the initial container before entry of the blood.

6. The process of claim 5 including the steps of adding a pre-conditioning portion of interferon into the stabilizing solution, and incubating the stabilized blood for a period of the order of two hours at a temperature about 37° C. before introducing said interferon inducer substance.

7. The process of claim 1 including the more detailed step of separating interferon containing plasma from the medium by centrifuging at a refrigerated temperature.

8. The process of claim 7 including the more detailed step of isolating interferon containing serum from the interferon containing plasma.

9. The process of claim 7 including the more detailed step of isolating interferon containing albumin from the interferon containing plasma.

10. The process of claim 1 including the step of separating the interferon as interferon containing plasma, and treating the plasma to remove inducer remnants therein.

11. The process of claim 10 wherein the removal of inducer is effected by passing the plasma through a body of immunosorbent containing immobilized anti-inducer antibodies.

12. The process of claim 10 wherein removal of the inducer is effected by dialysis.

13. The process of claim 10 wherein the removal of inducer is effected by adding active antibodies to the plasma, and precipitating the inducer as treated by the antibodies.

14. Said process of claim 1 wherein the blood is obtained from a human donor.

15. Said process of claim 13 wherein the blood is retroplacental.

16. Said process of claim 1 wherein the blood is obtained from a corpse.

17. Said process of claim 1 wherein the blood is obtained from an animal.

18. Said process of claim 17 wherein the blood is obtained after slaughter of the animal.

19. The process of claim 1 wherein the blood is agitated during the incubation step.

20. The process defined in claim 1 including the step of adding an antibacterial agent to the blood before incubation.

21. The process of claim 1 including the step of inoculating a donor from ten days to six weeks before blood is taken for the process with a substance inducing in-vivo antibodies thereby to produce an end product with a greater range of disease fighting capability.

22. The process of claim 21 including the more restricted innoculation step of innoculation with staphylococcal toxoid, E.coli bacteria or pseudomonas aeruginosa toxoid.

23. The process of claim 21 including the more restricted innoculation step of innoculation with a virus agent inducing antiviral antibodies.

24. The process of claim 23 wherein the interferon inducer and the agent are the same virus.

25. The process of claim 1 including the steps of removing plasma from the cultured blood and isolating interferon by use of an immunosorbent.

* * * * *